(12) United States Patent
Kohler et al.

(10) Patent No.: US 7,308,836 B1
(45) Date of Patent: Dec. 18, 2007

(54) APPARATUS AND METHOD FOR INSPECTING ARTICLES OF GLASSWARE

(75) Inventors: Timothy A. Kohler, Waterville, OH (US); William R. Martin, Slippery Rock, PA (US); Timothy McIntosh, Pittsburgh, PA (US); Gregory A. Ritz, Berkey, OH (US); Noel D. Wendt, Toledo, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 132 days.

(21) Appl. No.: 10/856,516

(22) Filed: May 28, 2004

(51) Int. Cl.
*G01M 19/00* (2006.01)
(52) U.S. Cl. .................................... 73/865.8
(58) Field of Classification Search ................ 73/865.8
See application file for complete search history.

(56) References Cited

U.S. PATENT DOCUMENTS

| | | | |
|---|---|---|---|
| 3,018,889 A | | 10/1956 | Fouse |
| 3,273,710 A | * | 9/1966 | Early et al. ............... 209/533 |
| 3,393,799 A | * | 7/1968 | Schmersal ................. 209/527 |
| 3,708,064 A | * | 1/1973 | Schepler et al. ........... 209/527 |
| 4,063,643 A | | 12/1977 | Wickstead |
| 4,468,277 A | | 8/1984 | Kontz |
| 4,724,948 A | | 2/1988 | Adams et al. |
| 4,912,318 A | * | 3/1990 | Kajiura et al. .......... 250/223 B |
| 6,581,751 B1 | * | 6/2003 | Nickey et al. .............. 198/379 |

FOREIGN PATENT DOCUMENTS

JP    356054306 A    5/1981

* cited by examiner

*Primary Examiner*—Daniel S. Larkin
*Assistant Examiner*—Nashmiya Fayyaz

(57) ABSTRACT

An apparatus for inspecting articles of glassware at a plurality of angularly spaced inspection stations includes a conveyor that moves articles of glassware to and from inspection stations, a drive roller that rotates articles of glassware at at least one inspection station, and an inspection device spaced from an inspection station and adapted to inspect an article of glassware as it is moved by the conveyor and caused to pass by the inspection device. A method for inspecting articles of glassware at a plurality of angularly spaced inspection stations includes the steps of moving the articles of glassware to and from the inspection stations, rotating the articles of glassware about an axis at at least one inspection station, inspecting the articles of glassware while they are rotating, stopping the rotation about the axis of the articles of glassware, moving the articles of glassware away from said at least one inspection station without rotating the articles of glassware about said axis, and inspecting the articles of glassware as they are moved.

28 Claims, 2 Drawing Sheets

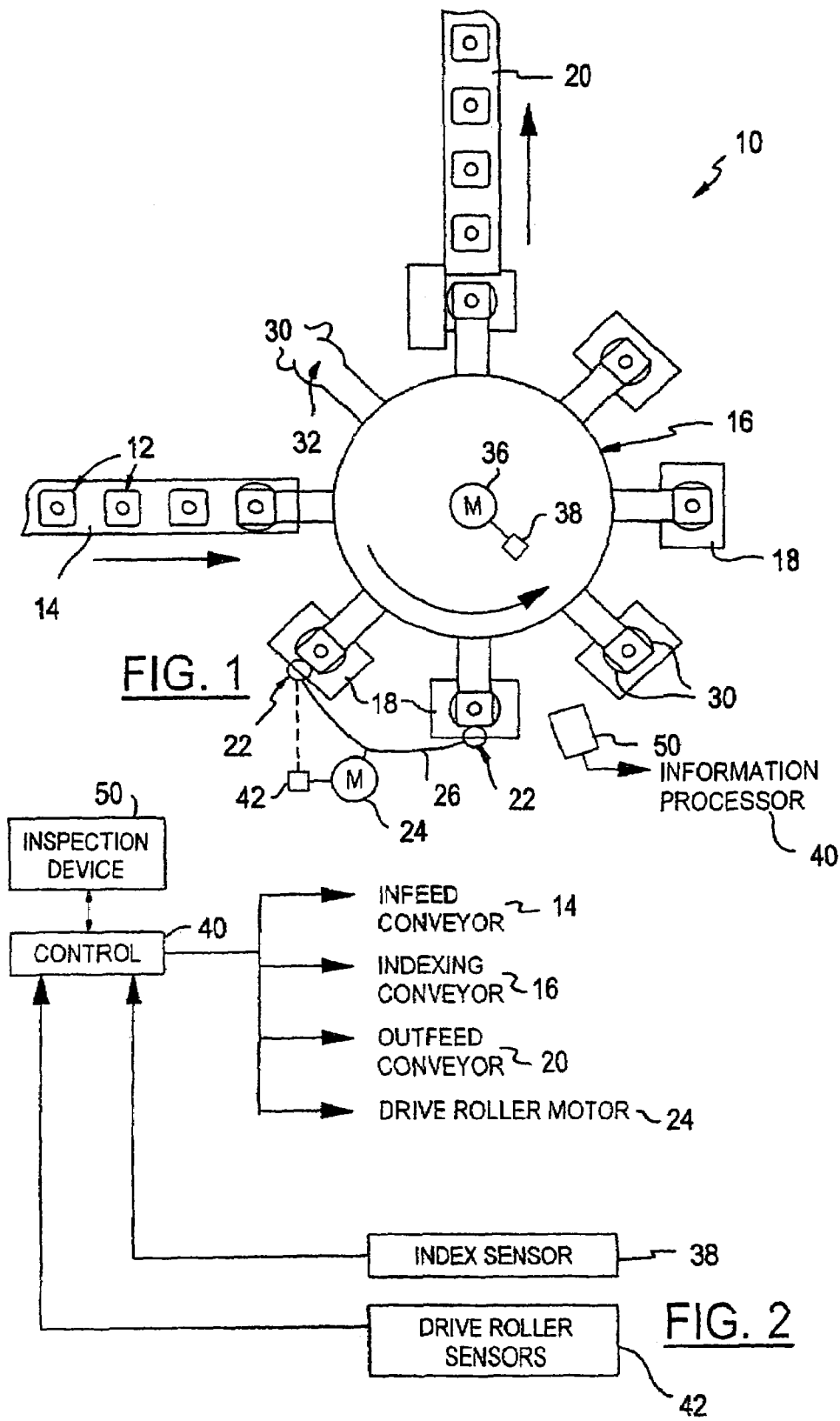

APPARATUS AND METHOD FOR INSPECTING ARTICLES OF GLASSWARE

FIELD OF THE INVENTION

This invention relates generally to an inspection system and more particularly to a method and apparatus for inspecting articles of glassware.

BACKGROUND OF THE INVENTION

In the manufacture of glassware, such as glass containers, various anomalies or variations can occur that affect commercial desirability of the containers. These anomalies, termed "commercial variations," can involve dimensional characteristics of the container such as the container finish, surface characteristics that can affect acceptable operation of the container, such as surface variations at the container sealing surface, or variations such as stones or checks within the container finish, sidewall or bottom.

It is conventional practice to mold indicia on each container indicative of the mold or origin of the container for inspection and quality control purposes. Some container inspection systems utilize a starwheel-type conveyor for accepting containers in sequence from a feed conveyor and transporting the containers through a series of inspection stations. One or more inspections may take place for each container at each station of the apparatus. The term "inspection" is used in its broadest sense to encompass any optical, electro-optical, mechanical or electrical observation or engagement with the container to measure or determine a potentially variable characteristic, including but not necessarily limited to mold codes and commercial variations.

SUMMARY OF THE INVENTION

An apparatus for inspecting articles of glassware at a plurality of inspection stations includes a conveyor that receives a plurality of articles of glassware, is rotatable to move each received article to and away from at least one inspection station, and is capable of discharging the received articles of glassware after they are inspected. The apparatus further includes at least one drive roller associated with at least one inspection station to rotate articles of glassware relative to the conveyor while the articles of glassware are at the associated inspection station, and an inspection device disposed adjacent to the conveyor and adapted to inspect an article of glassware as the article of glassware is moved by the conveyor and caused to pass by the inspection device. Desirably, one or more inspections may be performed on the container as it is rotated in the inspection station including the drive roller, and one or more additional inspections can be performed on the article of glassware as it is moved past the inspection apparatus by the conveyor to or from the inspection station.

In one preferred form, the drive roller is driven by a servo controlled motor so that the amount that an article of glassware is rotated by the drive roller can be determined to permit the rotational orientation of the article of glassware to be determined throughout the inspection process. Desirably, in one preferred form, the article of glassware is rotated at a plurality of inspection stations, with the rotational orientation of the container being tracked by a suitable controller throughout each and all of the inspection stations. Still further, in one presently preferred form, the apparatus includes more than one inspection device each preferably disposed downstream of an inspection station in which an article of glassware is rotated. Desirably, an article of glassware is rotated to present a first surface for inspection at a first inspection device, and is subsequent rotated to present another surface for inspection by a subsequent inspection device as the container progresses downstream during the inspection process.

A method of inspecting articles of glassware at a plurality of inspection stations includes the steps of rotating the articles of glassware about an axis at at least one inspection station, inspecting the articles of glassware while they are rotating, stopping the articles of glassware from rotating about the axis, moving the articles of glassware away from the inspection station at which they were rotated without rotating the articles of glassware about the axis, and inspecting the articles of glassware as they are moved. In one implementation, a glass container having a generally cylindrical neck and a body with generally flat, rectangular sides can be rotated at an inspection station to permit, among other things, inspection of the neck or finish of the container, and can then be moved by a conveyor to another inspection station with a subsequent inspection of at least a portion of at least one of the sides of the body being performed as the glass container is moved between inspection stations. Desirably, with control of the amount of rotation of the containers at each station different sides or portions of the body can be presented to different inspection devices as the container is moved among a plurality of inspection stations. Of course, other implementations, advantages, features and objects can be achieved through use of the above method and apparatus for inspecting articles of glassware, and an apparatus or method may attain all, some, or none of the objects, features or advantages.

BRIEF DESCRIPTION OF THE DRAWINGS

These and other objects, features and advantages of the present invention will be apparent from the following detailed description of the preferred embodiments and best mode, appended claims and accompanying drawings in which:

FIG. 1 is a diagrammatic view of an apparatus for inspecting articles of glassware according to one presently preferred embodiment of the invention;

FIG. 2 is a flow diagram of a control system that may be used with the inspection apparatus.

DETAILED DESCRIPTION OF THE PREFERRED EMBODIMENTS

Figure 3:
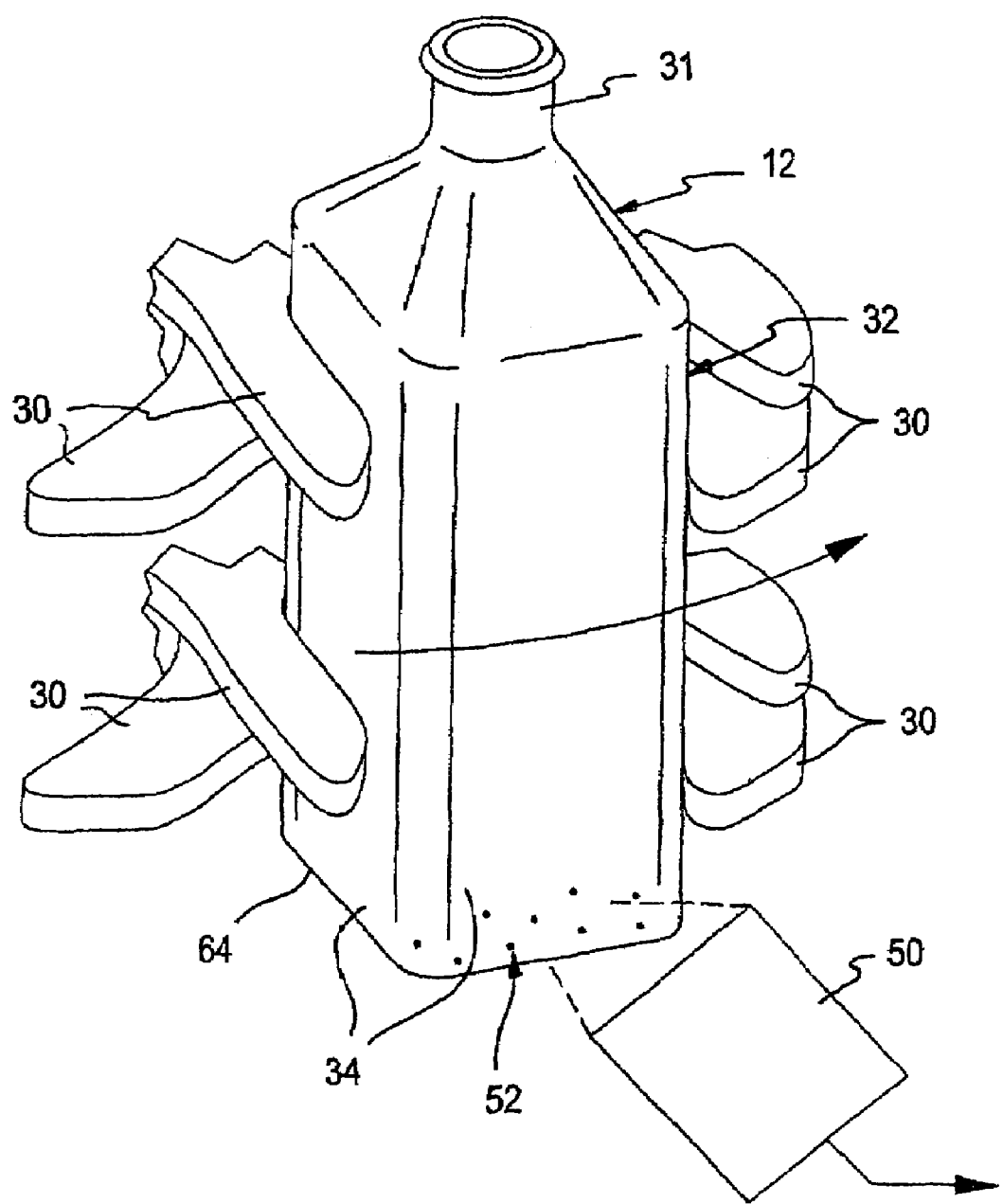
FIG. 3 is a fragmentary perspective view illustrating a portion of a conveyer of the inspection apparatus for transferring articles of glassware along an arc and past an inspection device.

Referring in more detail to the drawings, FIG. 1 illustrates an apparatus 10 for inspecting articles of glassware 12 including an infeed conveyor 14 supplying articles of glassware 12 to an indexing conveyor 16 that moves the articles of glassware 12 to and from consecutive inspection stations 18, and an outfeed conveyor 20 which takes articles of glassware 12 from the indexing conveyor 16 and transfers them for downstream processing. In one form, the indexing conveyor 16 is a starwheel-type conveyor that is rotated to move articles of glassware 12 among various angularly spaced inspection stations 18. At each inspection station 18, one or more inspections may be conducted to identify commercial variations, mold indicia, or other characteristic or feature of the articles of glassware 12. In at least some of the inspection stations, it is necessary or desirable to rotate the articles of glassware 12 about their central axis. To do so, a drive roller assembly 22 is provided at each station wherein rotation of the articles of glassware 12 is desired.

The apparatus 10 for inspecting articles of glassware, and the drive rollers 22 associated with at least one of the inspection stations 18, and preferably a plurality of inspection stations, may be constructed and arranged as disclosed in U.S. Pat. Nos. 6,557,695 and 6,581,751, the disclosures of which are incorporated herein by reference in their entirety. The inspection stations 18 preferably are equally angularly spaced around the perimeter of the inspection apparatus 10 and a wide range of inspections may take place at each or any of the inspection stations. In the preferred implementation of the invention, the containers are subject to inspection for commercial variations at at least some of the stations. Such inspection preferably comprises electro-optical inspection of container dimensional or other characteristics, such as shown in U.S. Pat. No. 2,682,802 (finish check detection), U.S. Pat. No. 3,880,750, U.S. Pat. No. 5,896,195 or EP 0961113 (sealing surface inspection), U.S. Pat. Nos. 4,378,493; 4,378,495; 4,584,469; 5,233,186; 5,291,271 or 5,637,864 (container sidewall inspection), or EP 0764846 (container bottom inspection). Successive containers can also be inspected to determine or read the code molded into the container for indicating container mold of origin, as illustrated for example in U.S. Pat. No. 4,644,151. Although electro-optical inspection techniques are currently preferred, the apparatus of the invention can also accommodate mechanical inspection techniques, such as illustrated in U.S. Pat. No. 5,414,939 in which the container is contacted by one or more rollers or fingers as it is rotated about its axis, and in U.S. Pat. No. 4,278,173 in which a gauge plug inspects the diameter of the container mouth. Electrical inspection techniques, as illustrated in U.S. Pat. No. 4,046,258, are also envisioned.

In at least some inspection stations 18 it is desirable to rotate the articles of glassware 12 about their central axis, and to conduct inspections while they are rotated. In one form, the articles of glassware 12 are rotated by a drive roller 22 that is pivoted relative to the inspection station 18 to selectively engage an article of glassware 12 at the inspection station 18. When engaged with an article of glassware 12, the drive roller 22 is driven for rotation to thereby rotate the article of glassware 12. The drive roller 22 is preferably driven by a servo controlled electric motor 24 to permit precise and consistent rotation of the articles.

When initially engaged by the drive roller 22, the article of glassware 12 is not rotating, and must be accelerated up to a desired rotational speed and then decelerated and stopped from rotating for subsequent transfer away from the inspection station 18 by the indexing conveyor 16. As shown in FIG. 1, in the presently preferred embodiment, a single motor 24 may be used to drive a pair of drive rollers 22, with each drive roller 22 associated with a separate inspection station 18. To do so, the motor 24 is coupled to the drive rollers 22 through a suitable drive system 26 preferably arranged so that each drive roller 22 is rotated in the same manner and at the same time to facilitate tracking the movement of the drive rollers 22. The drive system 26 connecting the motor 24 to the drive rollers 22 may be constructed and arranged as set forth in U.S. patent application Ser. No. 09/679,584 filed Oct. 4, 2000 and assigned to the assignee hereof, now U.S. Pat. No. 6,581,751.

The indexing conveyor 16 is preferably a starwheel-type conveyor including, as shown in FIGS. 1 and 3, a plurality of moveable fingers 30 adapted to selectively engage and release an article of glassware 12, such as a glass container. The fingers 30 are grouped together to define a plurality of pockets 32 with each pocket 32 adapted to receive a separate article of glassware 12. Desirably, each of a pair of independently moveable carriages include a plurality of fingers 30 such that movement of the carriages relative to each other causes the fingers to engage the articles 12 and release from the article 12, and movement of the carriages together causes movement of the article 12 with the conveyor 16. The fingers 30 may be received on a plurality of starwheels and the fingers and starwheels, may be configured to receive and transport articles of glassware 12 of varying sizes and shapes or the starwheels can be customized for particular shapes and sizes of articles of glassware. As shown in FIGS. 1 and 3, articles of glassware 12 having a generally cylindrical neck 31 and finish and a body 32 that is not round may be accommodated by the inspection apparatus 10. As shown in FIG. 3, the article of glassware 12 may have generally rectangular sides 34.

Desirably, the indexing conveyor 16 is driven by a servo controlled motor 36 to permit accurate and repeatable movement of the conveyor 16 and of the carriages for fast and efficient handling of the articles of glassware 12. One or more sensors 38 may be associated with one or both of the servo motor 36 driving the conveyor 16 and/or the conveyor 16 itself, to permit a controller 40 to determine and track the movement and orientation of the conveyor 16.

One or more sensors 42 are also preferably associated with one or both of the drive rollers 22 and the motor 24 that drives the drive rollers 22. These sensors 42 preferably communicate to the controller 40 the amount that the drive rollers 22 are rotated, and this information can be correlated to the amount that the articles of glassware 12 are rotated by the drive rollers 22. These sensors 42 may also communicate the position of the drive rollers 22 relative to an inspection station 18 and article of glassware 12 by communicating with the controller 40 whether the drive rollers 22 are advanced into an inspection station 18 for engagement with an article of glassware 12 or retracted away from the inspection station 18. The sensors 42 can further be used to determined the absence of an article of glassware 12 at an inspection station 18 which may be detected by over travel of the drive roller 22 when advanced into an inspection station 18 (i.e. travel of the drive roller 22 beyond the point where contact with an article of glassware 12 would occur if an article of glassware 12 were present at the inspection station 18).

A sensor 42 and/or the controller 40 may also detect absence of an article of glassware 12 at an inspection station 18 by way of monitoring the torque required to drive a drive roller 22. Absence of an article of glassware 12 at an inspection station 18 would be indicated by a reduced resistance to rotation, and hence, a reduced torque needed to drive the drive roller 22 at the inspection station 18 where the article of glassware 12 is absent. Detecting the absence of an article of glassware 12 at an inspection station 18 can be useful for example, without limitation, to detect articles of glassware 12 that become broken and can potentially damage the inspection apparatus 10, or to provide an indication that the inspection apparatus 10 is not functioning properly.

In a presently preferred embodiment, one or more inspection devices 50 are also interposed between adjacent inspection stations 18. The inspection devices 50 are disposed adjacent to the path of movement of the articles of glassware 12 when moved by the indexing conveyor 16 so that the articles of glassware 12 pass by the inspection devices 50 as they are transferred from one inspection station 18 to another by the conveyor 16. Desirably, the inspection devices 50 are constructed and arranged so that they perform one or more desired inspections as the articles of glassware are passed by the preferably stationary inspection device 50. For example, device 50 advantageously can be employed for reading mold indicia on the sidewall of a non-round container. As another example, devices 50 can be positioned between successive pairs of inspection stations for inspecting the sidewalls of non-round containers after the containers have been rotated 450° at the inspection station between the devices 50. As shown in FIG. 3, an inspection device 50 may detect mold indicia 52 provided on a side of a glass container, and as shown in FIG. 2, may relay or communicate the detected information to the controller 40 or information processor. Through use of the rotary indexing conveyor 16 as shown, the path of movement of the articles of glassware 12 relative to the inspection devices 50 is generally arcuate and the rate of movement of the articles of glassware 12 past the inspection devices 50 can be determined by use of appropriate sensors 38 associated with one or both of the servo motor 36 driving the conveyor 16 or sensors associated with the conveyor 16. Of course, inspections other than identifying mold indicia can be performed as the articles of glassware 12 are moved past the inspection devices 50.

Desirably, in one form wherein the inspection apparatus 10 is used with articles of glassware 12 having bodies that are not round, as shown for example in FIG. 3, the inspection devices 50 can be used to measure the width or other dimensions or characteristics of the articles of glassware 12 as they pass by without having to perform such inspections while the articles of glassware 12 are stopped from rotation at one of the inspection stations 18. This increases the efficiency and decreases the cycle time for inspection of the articles of glassware 12 at the inspection stations 18. Desirably, when an article of glassware 12 is engaged by the conveyor fingers 30 for transportation away from an inspection station 18, the article of glassware 12 is not rotating relative to the conveyor 16 and hence, is not rotating relative to an inspection device 50 passed which it is moved by the conveyor 16.

To inspect articles of glassware 12, the indexing conveyor 16 takes articles of glassware 12 from an infeed conveyor 14 and transfers them to various inspection stations 18 wherein a plurality of inspections can be performed. After the articles of glassware 12 are inspected, they are moved to an outfeed conveyor 20 for transport to a subsequent processing station, and articles of glassware 12 that have unacceptable commercial variations or are otherwise not desired to continue to a subsequent processing station can be rejected by a mechanism adjacent to or along the outfeed conveyor 20.

As previously noted, in at least some of the inspection stations 18 and the articles of glassware 12 are rotated about an axis of the articles for inspection. In the example wherein the articles of glassware 12 have a body 60 that is not round, such as shown in FIGS. 1 and 3, a drive roller 22 may be advanced into the inspection station to engage a generally cylindrical neck 31 or finish of the article of glassware 12. Rotation of the drive roller 22 causes rotation of the article of glassware 12, and the amount that the article of glassware 22 is rotated can be determined by the controller 40 as a function of the rotation of the drive roller 22, as previously set forth.

Hence, the rotational orientation of each article of glassware 12 can be tracked as the articles progress through the inspection apparatus 10. Desirably, in the presently preferred embodiment as shown, the articles of glassware 12 may be rotated so that after rotation they are offset 90° from the position at which they started to present a different portion or side of the articles for inspection by an inspection device 50 disposed between the inspection stations 18 when moved thereby by the conveyor 16. In this manner, after successive rotations at successive inspection stations 18, the entire circumference of an article of glassware 12 can be presented to a plurality of interposed inspection devices 50 when the articles are moved past the successive inspection devices 50. When the articles have a generally rectangular body 32 with a generally rectangular or square bottom or base 64 as shown in FIG. 3, any number of the sides of the article of glassware can be presented to respective inspection devices 50 to inspect the desired characteristics of the article.

Use of servo motors 24, 36 to drive the drive rollers 22, and to drive the indexing conveyor 16 enables accurate and repeatable movement of the articles of glassware 12 throughout the inspection apparatus 10. It also enables the rotational orientation of the articles of glassware 12, as well as the rotation orientation of the conveyor 16 relative to the inspection stations 18, to be determined and controlled for maximum efficiency in inspecting articles of glassware 12 both as they rotate, and as they are moved between inspection stations 18 by the conveyor 16.

Desirably, the information provided regarding the rotation of the drive rollers 22 and hence, the rotation of the articles of glassware 12 being rotated by the drive rollers 22, enables inspections to take place while the articles of glassware 12 are accelerated during initial rotation, and when they are decelerated and stopped for subsequent transfer. Information about the rotational orientation or position of the conveyor 16 relative to the inspection stations 18 can be relayed to the controller 40 or other information processor so that individual articles of glassware 12 and information obtained therefrom can be tracked as they are moved from station to station and eventually to the outfeed conveyor 20. Therefore, a wide range of inspections can be implemented while the articles of glassware 12 are rotated relative to the conveyor 16 and inspection stations 18, as well as when the articles of glassware 12 are moved between inspection stations 18 along the arc of travel caused by the rotary indexing conveyor 16. Desirably, the inspections can occur generally continuously throughout the movement of the articles of glassware 12 through the inspection apparatus, 10 and the apparatus 10 is capable of inspecting articles of glassware 12 at a high rate, for example, 300 articles of glassware per minute.

Those of ordinary skill in the art will recognize that the preceding description has been provided in terms of description rather than limitation. While presently preferred embodiment of the invention has been disclosed herein, modifications and substitutions can be made without departing from the spirit and scope of the invention set forth in the appended claims. For example, without limitation, the indexing conveyor can take on configurations other then that set forth, and the drive rollers may each be driven by separate motor, or by some other arrangement as desired. Still other modifications, and substitutions will be apparent to those skilled in the art in view of this disclosure.

The invention claimed is:

1. Apparatus for inspecting articles of glassware at a plurality of inspection stations, including:

a conveyor for communication with a supply of articles of glassware for sequential receipt of a plurality of articles of glassware, rotatable to move each received article of glassware to and away from inspection stations, and capable of discharging the received articles of glassware after the articles are inspected by one or more sensors at said inspection stations;

at least one drive roller associated with at least one of said inspection stations to rotate articles of glassware at said one inspection station relative to said conveyor while said articles of glassware are at said one inspection station and said conveyor is stationary; and an inspection device disposed adjacent to the conveyor, spaced in between said inspection stations and adapted to inspect an article of glassware as each article of glassware is being moved by the conveyor and caused to pass by said inspection device.

2. The apparatus of claim 1 wherein said conveyor includes at least one carrier selectively engaged with articles of glassware to permit the conveyor to move the articles of glassware, said at least one carrier being releasable from the articles of glassware to permit rotation of the articles of glassware relative to said at least one carrier by said at least one drive roller.

3. The apparatus of claim 2 wherein said at least one carrier engages the articles of glassware to move them relative to said inspection stations and holds the articles of glassware against rotation relative to the conveyor.

4. The apparatus of claim 1 wherein said conveyor is a starwheel conveyor having a plurality of pockets with each pocket adapted to receive a separate article of glassware and wherein said inspection stations are angularly spaced so that when rotated the starwheel conveyor moves articles of glassware relative to said inspection stations.

5. The apparatus of claim 1 which also includes a controller and wherein said at least one drive roller is driven by a servo-controlled motor that is communicated with said controller so that the rotational orientation of articles of glassware can be determined by said controller.

6. The apparatus of claim 5 wherein said conveyor is rotated by a servo-controlled motor that is communicated with said controller so that the position of the conveyor relative to the inspection stations can be determined.

7. The apparatus of claim 1 which includes a plurality of inspection stations at least some of which have a separate drive roller and a rotational inspection device that inspects articles of glassware as the articles of glassware are rotated in an inspection station by a drive roller, and said conveyor moves the articles of glassware to and from consecutive inspection stations and past said inspection device.

8. The apparatus of claim 7 which also includes a controller and wherein each drive roller is driven by a servo-controlled motor, and each servo-controlled motor is communicated with the controller to permit the controller to determine the rotational orientation of the articles of glassware as the articles of glassware are moved in and between inspection stations.

9. The apparatus of claim 5 which also includes at least one sensor operably associated with the drive roller and communicated with the controller to provide an indication of the amount of rotation of the driver roller to the controller.

10. The apparatus of claim 6 which also includes at least one sensor operably associated with the conveyor and communicated with the controller to provide an indication of the rotational position of the conveyor to the controller.

11. The apparatus of claim 1 which also includes a controller and wherein said conveyor is rotated by a servo-controlled motor that is communicated with said controller so that the rotational position of the conveyor relative to the inspection stations can be determined.

12. The apparatus of claim 11 which also includes at least one sensor operably associated with the conveyor and communicated with the controller to provide an indication of the rotational position of the conveyor to the controller.

13. The apparatus of claim 11 wherein said controller tracks the position of articles of glassware being moved by the conveyor as a function of the rotational position of the conveyor.

14. The apparatus of claim 13 wherein each inspection station includes at least one inspection apparatus used to inspect articles of glassware at said inspection stations, and each inspection apparatus and Inspection device is communicated with said controller so that the controller can correlate the data from the various inspections taking place at the inspection stations and the inspections taking place by way of said inspection device with the corresponding articles of glassware being inspected as the articles of glassware are moved among the inspection stations.

15. The apparatus of claim 1 wherein said conveyor moves the articles of glassware relative to said inspection stations and said at least one drive roller.

16. A method of inspecting articles of glassware at a plurality of inspection stations, including the steps of:

rotating the articles of glassware about an axis at at least one inspection station;

inspecting the articles of glassware with one or more sensors while the articles of glassware are rotating;

stopping the rotation about said axis of the articles of glassware;

moving the articles of glassware away from said at least one inspection station without rotating the articles of glassware about said axis; and inspecting the articles of glassware as the articles of glassware are being moved away from said at least one inspection station with an additional inspection device in between adjacent inspection stations.

17. The method of claim 16 wherein said stop of rotating the articles of glassware is accomplished with a drive roller that is driven by a servo-controlled motor and selectively engaged with an article of glassware to rotate the article of glassware, said servo motor providing information about the rotation to permit inspection of the article of glassware during a full rotational cycle of the article of glassware.

18. The method of claim 17 wherein the drive roller initially accelerates the article of glassware to a desired rotational speed, maintains the desired rotational speed for a predetermined period of time, and then decelerates the rotation of the article of glassware until the article of glassware stops rotating, and said servo-controlled motor permits tracking of the rotational orientation of the article of glassware throughout rotation of the article of glassware so that the article of glassware can be inspected throughout rotation of the article of glassware.

19. The method of claim 16 wherein said moving step is accomplished with a rotary conveyor that moves the articles of glassware to and from angularly spaced inspection stations.

20. The method of claim 16 which also includes the step of providing information obtained from each inspection of an article of glassware to a controller, and correlating the information obtained by the controller with the article of glassware from which the information was obtained.

21. The method of claim 19 which also includes the step of tracking the location of an article of glassware relative to the inspection stations and correlating the information obtained from each of said inspecting steps with an article of glassware being inspected.

22. The method of claim 16 wherein said step of inspecting said articles of glassware as the articles of glassware are moved is accomplished by passing said articles of glassware by said inspection device.

23. The method of claim 16 wherein said step of inspecting said articles of glassware as the articles of glassware are moved is accomplished by passing said articles of glassware by said inspection device along an arcuate path.

24. The method of claim 23 wherein said articles of glassware are passed by said inspection device without rotation of the articles of glassware about said axis.

25. Apparatus for inspecting articles of glassware at a plurality of angularly spaced inspection stations, including:
- a rotary conveyor in communication with a supply of articles of glassware for sequential receipt of a plurality of articles of glassware, rotatable to move each received article of glassware to and away from inspection stations, and capable of discharging the received articles of glassware after the articles are inspected by one or more sensors at said inspection stations;
- at least one drive roller driven for rotation by a servo-controlled motor and associated with at least one of said inspection stations to rotate articles of glassware at said one inspection station relative to said conveyor while said articles of glassware are at said one inspection station and said conveyor is stationary;
- an inspection device disposed adjacent to the conveyor, spaced in between said inspection stations and adapted to inspect an article of glassware as each article of glassware is being moved by the conveyor and caused to pass by said inspection device; and
- a controller communicated with said at least one drive roller so that the rotational orientation of articles of glassware rotated by said at least one drive roller can be determined by said controller.

26. The apparatus of claim 25 which also includes a sensor operably associated with said at least one drive roller and said controller to provide information relating to the rotation of the drive roller to the controller.

27. The apparatus of claim 25 wherein said conveyor is rotated by a servo-controlled motor that is communicated with said controller so that the position of the conveyor relative to the inspection stations can be determined.

28. The apparatus of claim 25 which also includes at least one sensor operably associated with the conveyor and the controller to provide information relating to the rotational orientation of the conveyor to the controller.

* * * * *